US00PP09556P

United States Patent [19]

Tachibana et al.

[11] Patent Number: Plant 9,556

[45] Date of Patent: May 21, 1996

[54] PETUNIA PLANT NAMED 'REVOLUTION PINKMINI'

[75] Inventors: Ryuichi Tachibana, Yamato; Yuji Tamura, Kofu; Ushio Sakazaki, Hikone, all of Japan

[73] Assignee: Suntory Limited, Osaka, Japan

[21] Appl. No.: 369,324

[22] Filed: Jan. 6, 1995

Related U.S. Application Data

[63] Continuation of Ser. No. 234,619, Apr. 28, 1994, abandoned, which is a continuation of Ser. No. 90,268, Jul. 13, 1993, abandoned.

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |

*Primary Examiner*—James R. Feyrer

*Attorney, Agent, or Firm*—Burns, Doane, Swecker & Mathis

[57] ABSTRACT

Disclosed herein is a decumbent type petunia plant having a long stem. The plant has abundant branching and a great profusion of blooms, and the whole bush remains in bloom for a long period of time. The flowers are single and small, and petals have a vivid reddish purple color and deep purple lines radiating from a pinkish white throat portion. The plant is highly resistant to rain, drought, heat, and disease.

4 Drawing Sheets

This application is a continuation of application Ser. No. 08/234,619, filed Apr. 28, 1994 which is a continuation application of Ser. No. 08/090,268, filed Jul. 13, 1993, both now abandoned.

BACKGROUND OF THE VARIETY

The present invention relates to a new and distinct variety of petunia plant obtained from crossing a line designated 'Cloud Pink' from, within the 'Cloud Mixed' series and a wild type of petunia plant (♂) having white color petals, native to Brazil.

Petunia is a very popular plant and is used for flower bedding and potting in the summer season. There are only a few varieties of the petunia plant which do not have an upright growth habit and which have a high resistance to rain, heat, drought and cold. The Petunia series 'Revolution' which we patented which includes the plants 'Revolution Purplepink', U.S. Plant Pat. No. 6,915; 'Revolution Brilliantpink', U.S. Plant Pat. No. 6,914; and 'Revolution Brilliantpink — Mini', U.S. Plant Pat. No. 6,899, are petunia plants having decumbent growth of branches, with long stems, a lower spreading habit, abundant branching and high resistance to heat, drought, and rain. However, there are only a few varieties having a wide range of a flower color. Accordingly, this invention was aimed to obtaining a new variety having a vivid reddish purple color, together with features of said 'Revolution' series.

The new variety of petunia plant according to this invention originated from a crossing of 'Cloud Pink', having a pink petal coloration obtained as a line from within the 'Cloud Mixed' series available from T & M Limited of England as the female parent and a wild type of petunia plant native to Brazil having white color petal as the pollen parent, in February, 1989 at the Plant Biotechnology Laboratory, Institute for Fundamental Research of SUNTORY Ltd., located at 2913-1 Torihara, Hakushu-cho, Kitakoma-gun, Yamanashi-ken, Japan. From this crossing 350 seedlings were obtained in 1989, from which 8 seedlings were selected, propagated by cutting, and then grown as a trial by flower bedding and potting from the spring of 1990. Only two of the 8 resulting plants were selected. The botanical characteristics of the finally-selected plants were then examined, using a similar variety, 'Revolution Brilliantpink-mini', for comparison, from the spring of 1991. These two plants were found to exhibit different phenotypical characteristics. One of these plants exhibited dissimilar vivid red flowers and is not claimed herein. The other plant is claimed herein and is distinguishable from any other variety, whose existence is known to us, and this new variety of petunia plant was named 'Revolution Pinkmini'.

In the following description, the color-coding is in accordance with the Horticultural Color Chart of The Royal Horticultural Society, London, England (R.H.S. Color Chart), and the Inter-Society Color Council-Nation Bureau of Standards Color Name (I.S.C.C.-N.B.S. Color Name). A color chart based on The Japan Color Standard for Horticultural Plant (J.H.S. Color Chart) is also added for reference.

The female parent used in the breeding of 'Revolution Pinkmini' is 'Cloud Pink' having pink petal coloration from within the 'Cloud Mixed' series available from T&M Limited of England. This petunia plant in world wide marketed. The main botanical characteristics of this female parent are as follows.

Plant:

*Growth habit.*—Upright.

*Plant height.*—30–40 cm.

*Spreading area of plant.*—25–35 cm in diameter.

*Blooming period.*—April to September, the southern Kanto area, Japan.

Stems:

*Thickness.*—3.0–6.0 mm.

*Anthocyanin pigmentation.*—Absent.

*Branching.*—Abundant.

*Pubescence.*—Medium.

*Length of internodes.*—2.0–4.0 cm.

Leaf:

*Leaf attaching angle.*—Horizontal.

*Shape.*—Elliptic.

*Size (average).*—5.0–6.5 cm in length; 2.5–3.5 cm in width.

*Thickness.*—0.4–0.6 mm.

*Color.*—Moderate olive green to moderate yellow green (R.H.S. 146A–137C, J.H.S. 3508–3712).

*Pubescence.*—Medium.

Flower: Opening obliquely upward.

*Type.*—Single.

*Shape.*—Funnel-shape, having corolla with five fused segments or petals.

*Diameter.*—8–10 cm.

*Color.*—Red purple (R.H.S. 73A–73B).

*Reproductive organs.*—1 normal pistil having a stigma and 5 normal stamens.

*Peduncle.*—1.5–2.5 mm in thickness, and 2.5–3.0 mm in length.

Physiological and ecological characteristics: Moderate resistance to rain, heat and disease, and moderate resistance to pests.

The pollen parent used in the breeding of 'Revolution Pinkmini' is a wild type of petunia native to Brazil having white color petals, the seeds of which were gathered at Gramado, Rio Grande Do Sul, Brazil and introduced to Japan in October, 1983. This wild type of plant is presently maintained at the aforementioned Plant Biotechnology Laboratory, SUNTORY, Ltd. The main botanical characteristics of this male parent are as follows.

Plant:

*Growth habit.*—Decumbent.

*Plant height.*—20 cm.

*Spreading area of plant.*—100–150 cm in diameter.

*Blooming period.*—May to August in the southern Kanto area, Japan.

Stems:

*Length from base.*—50–80 cm.

*Thickness.*—Main stem 2.0–3.0 mm; lateral stem 1.5–2.5 mm.

*Color.*—Strong yellow green (R.H.S. 144B–144C, J.H.S. 3512–3513).

*Branching.*—Over-abundant.

*Pubescence.*—Heavy.

*Length of internodes.*—1.0–2.0 cm before blooming; 1.5–3.0 cm during blooming.

Leaf:

*Phyllotaxis.*—Opposite both before and during blooming.

*Shape.*—Oval.

*Size (average).*—4.5–5.5 cm×2.5– 3.5 cm.

*Thickness.*—0.4–0.5 mm.

*Color.*—Grayish olive green (R.H.S. 137A–137B, J.H.S. 3716–3717).

*Pubescence.*—Scant.

Flower: Opening obliquely upward.

*Type.*—Single.

*Shape.*—Funnel-shape, having corolla with five fused segments or petals.

*Diameter.*—4.0–5.0 cm.

*Color.*—In the unopened stage (bud), yellow green (R.H.S. 149C–149D, J.H.S. 3303–3304); when open, green white (R.H.S. 157D, J.H.S. 3102); at full bloom, white (R.H.S. 155D, J.H.S. 2902).

*Reproductive organ.*—1 pistil and 5 stamens, both normal.

*Peduncle.*—0.9–1.2 mm in thickness, and 2.0–2.5 mm in length.

Physiological and ecological characteristics: High resistance to cold, relatively high resistance to heat, and moderate resistance to diseases and pests.

This new and distinct variety of petunia plant, 'Revolution Pinkmini', was asexually reproduced by cuttings at the aforementioned Plant Biotechnology Laboratory, Institute for Fundamental Research of SUNTORY Ltd., residing at 2913-1 Torihara, Hakushu-cho, Kitakoma-gun, Yamanashi-ken, Japan, and the homogeneity and stability thereof were confirmed.

SUMMARY OF THE VARIETY

The new variety of petunia plant has a decumbent habit and long stem, and thus is very different from similar variety, 'Falcon Rose', having an semi-upright growth habit and 'Revolution Brilliantpink-mini'. The plant has abundant branching and great profusion of blooms, and the whole bush remains in bloom for a considerable period of time, longer than the bloom period of 'Falcon Rose'. The flowers are single, and smaller than 'Falcon Rose', the patent have vivid reddish purple color petals and moderate purple lines in corolla radiating from pinkish white throat portion, which is clearly distinguished from 'Revolution Brilliantpink-mini', having strong reddish purple color petals. The plant is highly resistant to rain, drought, and heat and disease.

DESCRIPTION OF THE VARIETY

Figure 1:
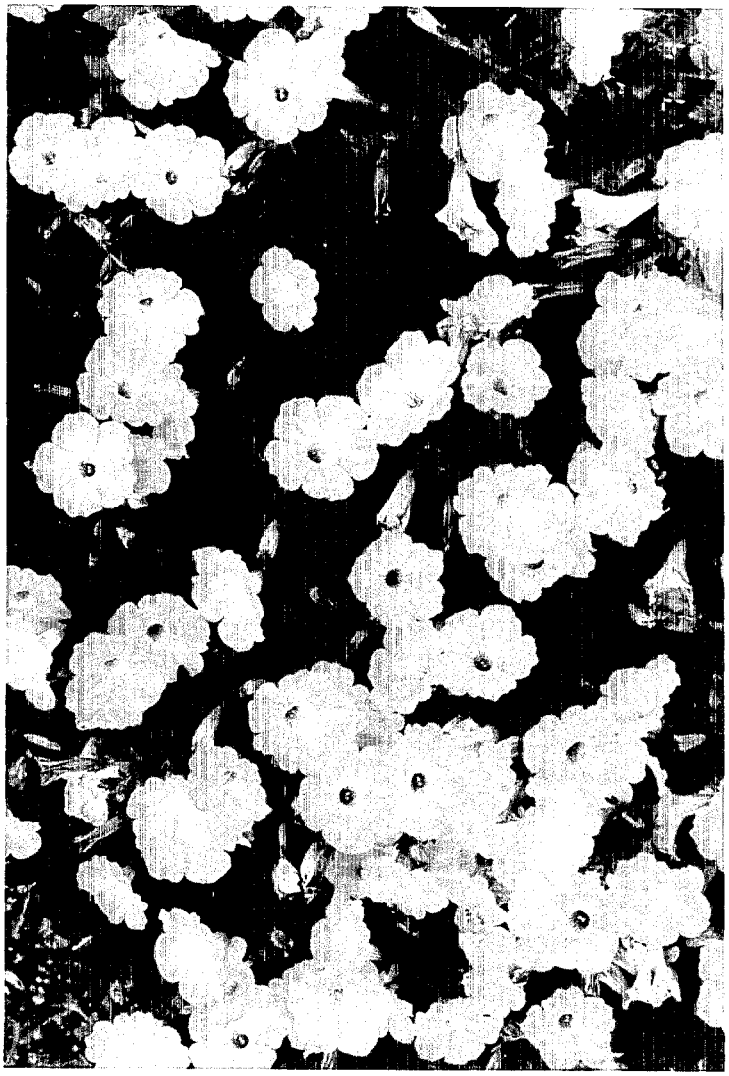
FIG. 1 is a photograph giving a partial view of the new variety of petunia plant planted in a flower bed.
Figure 2:
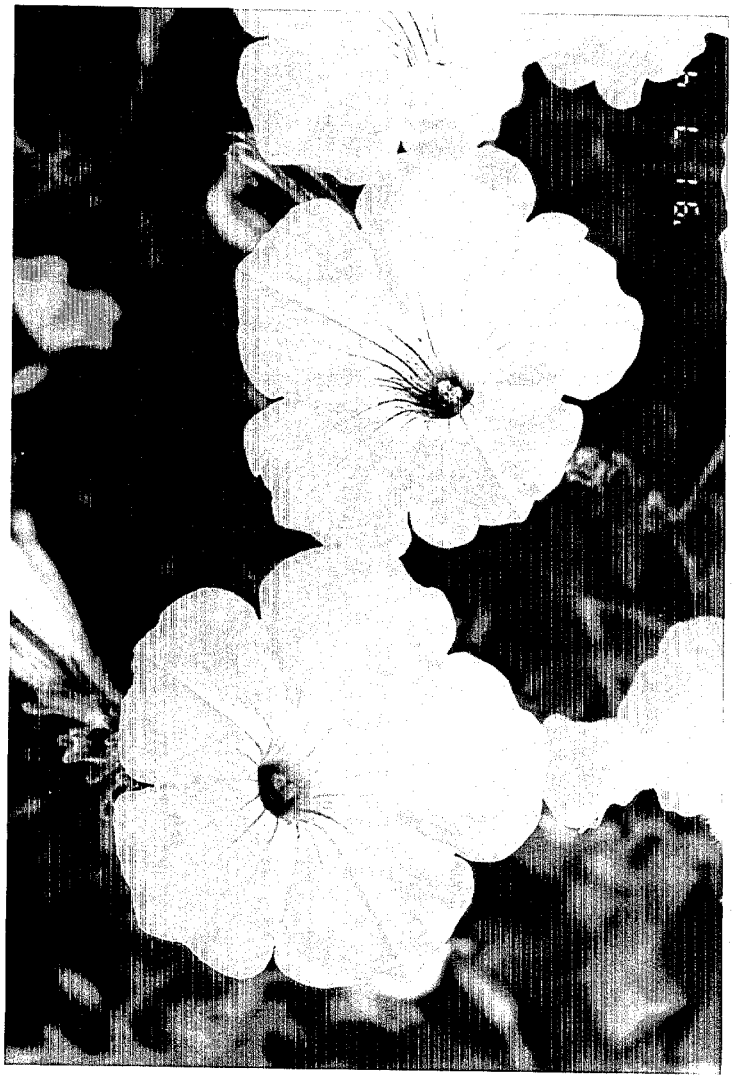
FIG. 2 is a photograph of flowers of the new variety of petunia plant.
Figure 3:
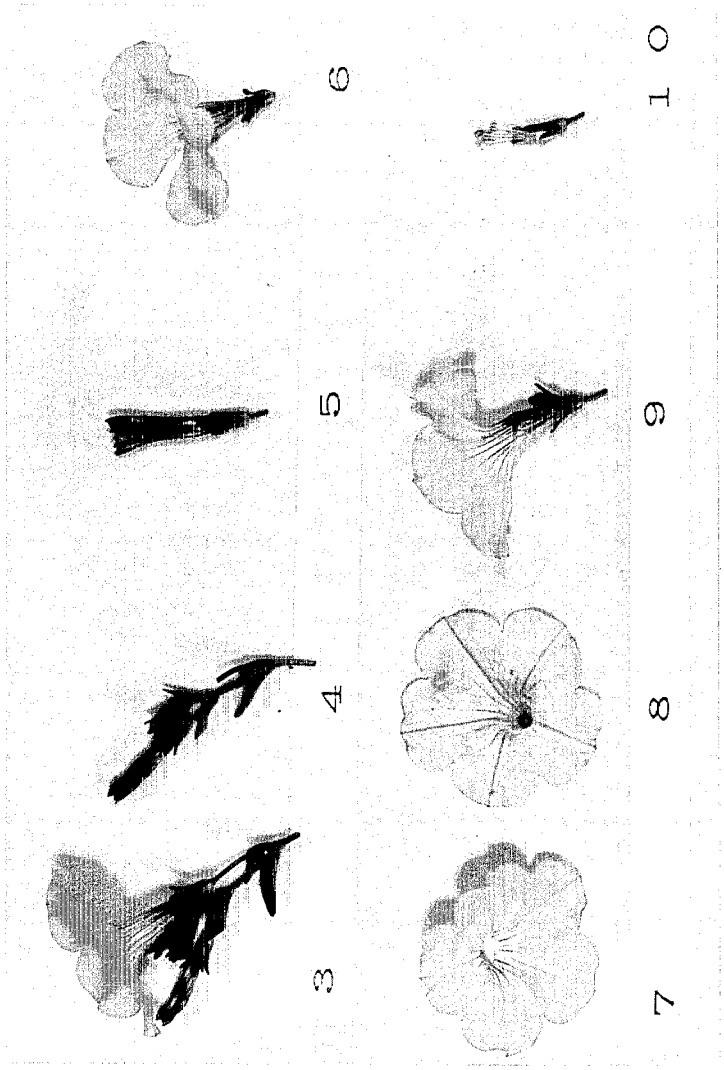
FIG. 3 is a photograph showing, in numerical order, a branch having an open flower (3), a current shoot (4), a bud (5), a side view of the flower (6), a front view of the flower (7), a rear view of the flower (8), an interior view of the flower (9), and pistil and stamens (10), of the new variety of petunia plant.
Figure 4:
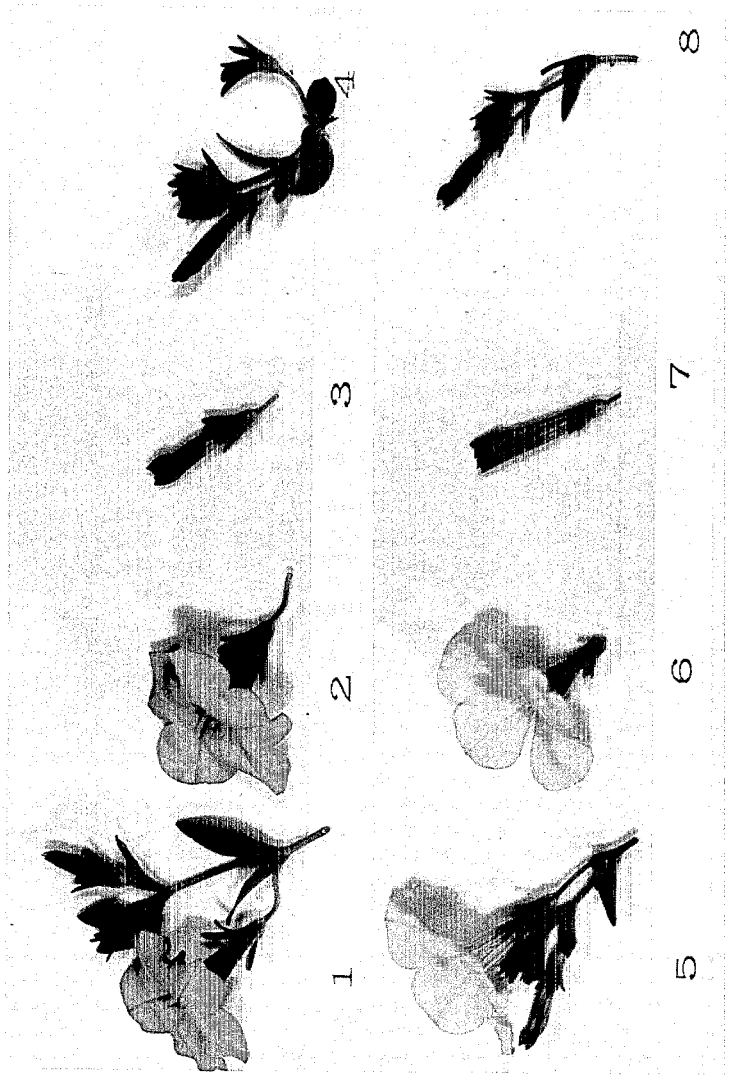
FIG. 4 is a photograph showing, in numerical order, a brunch having an open flower (1), a flower (2), a bud (3), and a current shoot (4) of a similar variety 'Revolution Brilliant-pink-mini', in comparison with corresponding items (5–8) of the new variety of petunia plant.

The botanical characteristics of the new and distinct variety of petunia plant 'Revolution Pinkmini' are as follows.

Plant:

*Growth habit.*—Decumbent. The stems hang down when potted in a hanging pot.

*Plant height.*—20–25 cm.

*Spreading area of plant.*—The stem extends to a length of 60–75 cm from the base, and thus the spreading area of the plant is 120–150 cm in diameter.

*Growth.*—Very vigorous with abundant branching, a great profusion of blooms; the whole bush remaining in bloom for a considerable period of time.

*Blooming period.*—Late March to the beginning of October, in all areas of Japan. The plant shape does not change throughout this period.

Stems: Extending to 60–75 cm.

*Thickness.*—3.0–4.5 mm.

*Anthocyanin pigmentation.*—Absent.

*Pubescence.*—Medium.

*Branching.*—Over-abundant (primary), abundant (secondary).

*Length of internode.*—2.0–4.0 cm.

Leaf:

*Leaf attaching angle.*—Horizontal, slightly upward.

*Shape.*—Oval.

*Length.*—3.5–4.5 cm.

*Width.*—2.5–3.5 cm.

*Thickness.*—0.4–0.6 cm.

*Color.*—Moderate olive green (R.H.S. 146A, J.H.S. 3509).

*Pubescence.*—Medium.

Flower: Opening obliquely upward.

*Type.*—Single.

*Shape.*—Funnel-shape, having corolla with five fused segments or petals.

*Diameter.*—5.0–6.0 cm.

*Color.*—Vivid reddish purple (R.H.S. 73B, J.H.S. 9206), moderate purple (R.H.S. 83A, J.H.S. 8609) line in corolla radiating from pinkish white (R.H.S. 69D, J.H.S. 9201) throat inside portion.

*Reproductive organs.*—1 normal pistil and 5 normal stamens (2 stamens are higher than pistil). The pistils and stamens are typical of the genus. The new variety is both male and female fertile.

*Peduncle.*—2.0–2.5 mm in thick, and 0.2–0.3 cm in length.

*Ploidy.*—The new variety is believed to be diploid consistent with the diploid character of its parents.

Physiological and ecological characteristics: High resistance to drought, rain, and heat. Also high resistance to diseases. Moderate resistance to pests.

This new variety of petunia plant is most suitable for flower bedding and potting, particularly in hanging pots or planters, and further excellent for ground cover. When good soil conditions are present with adequate moisture, the new variety spreads by the rooting of the nodes of stems.

The plant of this new variety 'Revolution Pinkmini' is presently planted and maintained at the Plant Biotechnology Laboratory, Institute for Fundamental Research of SUNTORY Ltd., residing at 2913-1 Torihara, Hakushu-cho, Kitakoma-gun, Yamanashi-ken, Japan.

We claim:

1. A new and distinct variety of petunia plant, substantially as herein illustrated and described, characterized particularly as to novelty by (A) being a decumbent habit plant having long stems, (B) an abundant branching and a great profusion of blooms, the whole bush remaining in bloom for a considerable period of time, (C) flowers that are single and small, the petals having a vivid reddish purple color and moderate purple lines in corolla radiating from pinkish white throat inside portion, and (D) a high resistance to rain, drought, heat, and disease.

* * * * *